United States Patent [19]

Wu et al.

[11] 3,962,252
[45] June 8, 1976

[54] 10-IMIDOYLACRIDANS

[75] Inventors: Yao Hua Wu; Walter G. Lobeck, Jr., both of Evansville, Ind.

[73] Assignee: Mead Johnson & Company, Evansville, Ind.

[22] Filed: Mar. 24, 1975

[21] Appl. No.: 561,462

Related U.S. Application Data

[62] Division of Ser. No. 336,671, Feb. 28, 1973, Pat. No. 3,888,852.

[52] U.S. Cl. .............................. 260/279 R; 424/248; 424/257; 260/240 G
[51] Int. Cl.² ................ C07D 219/14; C07D 401/04
[58] Field of Search ..................... 260/279 R, 240 G

[56] References Cited
UNITED STATES PATENTS

| | | | |
|---|---|---|---|
| 3,498,986 | 3/1970 | Meisels et al. | 260/279 R |
| 3,770,727 | 11/1973 | Brack | 260/240.8 |

OTHER PUBLICATIONS

Moskoukina et al, Chemical Abstracts, vol. 73, 14,649n (1970).

*Primary Examiner*—Alton D. Rollins
*Assistant Examiner*—Diana G. Rivers
*Attorney, Agent, or Firm*—Robert H. Uloth; Robert E. Carnahan

[57] ABSTRACT

Novel 10-imidoylphenoxazines and 10-imidoylacridans are prepared by reacting a phenoxazine or acridan having optional substituents selected from the group consisting of trifluoromethyl, halogen, dihalogen, alkyl or alkoxy with an imidoyl halide prepared in situ from amides and lactams. Illustrative embodiments are 10-(5-methyl-1-pyrrolin-2-yl)phenoxazine and 9,9-dimethyl-10-(5-methyl-1-pyrrolin-2-yl)acridan. The imidoylphenoxazine and imidoylacridan products are generally useful as smooth muscle relaxants.

7 Claims, No Drawings

10-IMIDOYLACRIDANS

CROSS-REFERENCE TO RELATED APPLICATION

This application is a division of copending application Ser. No. 336,671, filed Feb. 28, 1973 now U.S. Pat. No. 3,888,852.

BACKGROUND OF THE INVENTION

This invention pertains to heterocyclic carbon compounds which have drug and bio-affecting properties. In particular, this invention relates to 10-imidoylphenoxazines and 10-imidoylacridans effective as smooth muscle relaxants. The term "smooth muscle relaxant" has a definite meaning in pharmacology and medicine. It generally refers to agents known to relax smooth muscle in blood vessels, in the bronchial tree and in the gastrointestinal, biliary, urinary and uterine tracts. Two types of smooth muscle relaxants are known; namely, those that produce their effect by direct action on smooth muscle (e.g., papaverine or aminophylline) and those that produce their action primarily via the autonomic nerve supply (e.g., isoproterenol and atropine). The compounds of the instant invention are thought to be direct acting. Another feature of the invention is a therapeutic process for producing smooth muscle relaxant effects in mammals by administration of the 10-imidoylphenoxazines and 10-imidoylacridans.

We have previously disclosed 10-imidoylphenothiazines in our co-pending United States patent application Ser. No. 147,667 filed May 27, 1971, now U.S. Pat. No. 3,719,671, as being of interest for their intestinal relaxant and antithrombogenic activity. We have now unexpectedly discovered that another class of amidines, namely 10-imidoylphenoxazines and 10-imidoylacridans and their salts, have smooth muscle relaxant activity and, in some instances, antithrombogenic activity.

SUMMARY OF THE INVENTION

This invention is broadly concerned with a group of amidines incorporating phenoxazine and acridan heterocycles. More particularly, the invention pertains to 10-imidoylphenoxazines and 10-imidoylacridans of Formula I and non-toxic pharmaceutically acceptable acid addition salts thereof.

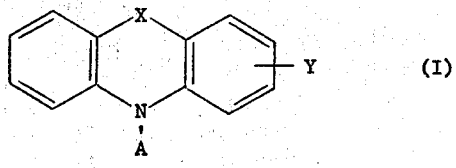

The substances represented by Formula I are novel compositions of matter and are useful as smooth muscle relaxants and, in some instances, as inhibitors of platelet aggregation in mammals.

In Formula I, X represents oxygen or a divalent methylene radical of the formula $-C(Z_1Z_2)-$. Substituents $Z_1$ and $Z_2$ of the methylene radical are independently selected from hydrogen or straight chain lower alkyl of from 1 to 4 carbon atoms inclusive.

The phenoxazine or acridan substituent "Y" represents a member of the group consisting of hydrogen, trifluoromethyl, halogen, dihalogen, lower alkyl of 1 to 4 carbon atoms inclusive and lower alkoxy 1 to 4 carbon atoms inclusive.

A is a substituent selected from the group consisting of an imidoyl moiety represented by

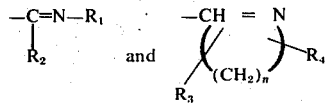

wherein $n$ signifies an integer of 3 to 5, $R_1$ represents a member of the group consisting of lower alkyl of 1 to 4 carbon atoms inclusive and cycloalkyl of 3 to 6 carbon atoms inclusive; $R_2$ represents hydrogen or lower alkyl of 1 to 4 carbon atoms inclusive; $R_3$ and $R_4$ are members independently selected from the group consisting of hydrogen or lower alkyl of 1 to 4 carbon atoms inclusive. It is to be understood that by the terms "lower alkyl" and "lower alkoxy" as used herein, it is meant that the carbon chain which comprises these groups include both straight and branched carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl. By the term "straight chain lower alkyl" as used herein it is meant that the carbon chain is a member of the group comprised of methyl, ethyl, propyl, and n-butyl radicals. By the term "independently selected" as used herein, it is meant that the $R_3$ and $R_4$ substituents may or may not be identical. By the term "halogen" as used herein, it is meant to connote all members of that group, i.e., chlorine, bromine, fluorine, and iodine.

The compounds of Formula I are basic and in some instances crystalline compounds, which are practically insoluble in water, but have substantial solubility in most organic solvents and in aqueous solutions of organic or inorganic acids. Conversion of the imidoylphenoxazine and imidoylacridan bases of Formula I to corresponding non-toxic pharmaceutically acceptable acid addition salts is accomplished by admixture of the base with a selected acid in an inert organic solvent such as ethanol, benzene, ethyl acetate, ether, halogenated hydrocarbons and the like. It is to be understood that, as used herein, the term "non-toxic pharmaceutically acceptable acid addition salt" refers to a combination of a compound of Formula I with a relatively non-toxic inorganic or organic acid, the anion of which is pharmaceutically ineffective in the usual dosage.

Examples of inorganic or organic acids which may be employed to provide non-toxic pharmaceutically acceptable acid addition salts of the substances of Formula I are: sulfuric, phosphoric, hydrochloric, hydrobromic, hydroiodic, sulfamic, acetic, lactic, maleic, succinic, malic, fumaric tartaric, citric, gluconic, glutaric, ascorbic, benzoic, cinnamic, methanesulfonic, para-toluenesulfonic, isethionic, and related acids.

A preferred method of salt preparation is to treat the Formula I base with substantially one chemical equivalent of hydrogen chloride in ethanol solution. The imidoylphenoxazine or imidoylacridan salt precipitates from ethanolic solution upon the addition of anhydrous ether or chilling. Both the free base and salt forms of the products of Formula I are useful for the purposes of the invention although salts are particularly preferred because of their general water solubility.

It will be apparent to those skilled in the art that the amidines of Formula I can exist as stereoisomeric modifications when as asymmetric center is present. For example, in the case of a compound of Formula I wherein the "substituent A" is a pyrrolinyl moiety containing a $R_3$ or $R_4$ substituent other than hydrogen such as 2-chloro-10-(5-methyl-1-pyrrolin-2-yl)phenoxazine, an asymmetric center is present resulting in a racemic modification. Resolution of a racemic modification may be carried out according to conventional procedures by using appropriate optically active acids. It is to be understood that all stereoisomeric forms of the compunds of Formula I are considered to be within the purview of this invention.

The imidoyl phenoxazines and imidoyl acridans reference): the present invention characterized by Formula I are prepared by a process which comprises reacting a phenoxazine or acridan having Formula II

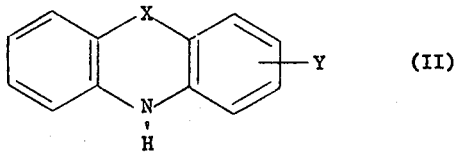

with a reactant selected from the group consisting of carboxamides of the formulas

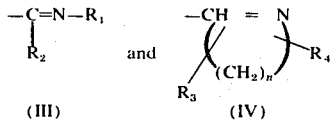

in the presence of phosphorus oxychloride in a suitable inert organic solvent. The symbols "X" and "Y" in the heterocyclic reactant of Formula II and $R_1$, $R_2$, $R_3$, $R_4$, and $n$ in the carboxamide reactant have the meanings hereinabove described for Formula I.

Suitable carboxamide reactants, by way of example, are:
N-alkylformamides such as:
N-methylformamide,
N-ethylformamide,
N-n-propylformamide,
N-isopropylformamide,
N-n-butylformamide,
N-tert.-butylformamide;
N-alkylcarboxamides such as:
N-methylacetamide,
N-methyl-2-methylpropionamide,
N-methylvaleramide,
N-isopropylacetamide;
N-cycloalkylformamides such as:
N-cyclopropylformamide,
N-cyclobutylformamide,
N-cyclopentylformamide,
N-cyclohexyformamide;
N-cycloalkylcarboxamides such as:
N-cyclopropylacetamide,
N-cyclohexylacetamide,
N-cyclopentyl-2-methylpropionamide.

In addition, cyclic carboxamides (lactams) can also be employed and include, for example:
2-pyrrolidinone,
5-methyl-2-pyrrolidinone,
5,5-dimethyl-2-pyrrolidinone,
3-methyl-2-pyrrolidinone,
4-methyl-2-pyrrolidinone,
5,5-di-n-butyl-2-pyrrolidinone,
2-oxohexamethyleneimine,
2-piperidone,
6-methyl-2-piperidone,
6,6-dimethyl-2-piperidone.

Suitable phenoxazines are:
phenoxazine,
2-(trifluoromethyl)phenoxazine,
2-chlorophenoxazine,
3-chlorophenoxazine,
4-chlorophenoxazine,
2-bromophenoxazine,
2,3-dichlorophenoxazine,
3,4-dichlorophenoxazine,
2-methoxyphenoxazine,
4-methoxyphenoxazine,
4-isopropoxyphenoxazine,
2-methylphenoxazine,
4-methylphenoxazine.

Suitable acridans are:
acridan,
2-chloroacridan,
4-chloroacridan,
2-methoxyacridan,
4-methoxyacridan,
2-(trifluoromethyl)acridan,
4-(trifluoromethyl)acridan,
2-methylacridan,
4-n-butylacridan,
9,9-dimethylacridan,
2-chloro-9,9-dimethylacridan,
9,9-dimethyl-2-(trifluoromethyl)acridan,
9,9-dimethyl-4-methoxyacridan,
9-methyl-2-(trifluoromethyl)acridan,
9-ethyl-9-methylacridan,
9,9-di-n-butylacridan.

In carrying out the process for the preparation of the substances of Formula I, approximate stoichiometric portions of the phenoxazine or acridan heterocycle and appropriate carboxamide and phosphorus oxychloride are mixed together in an inert aprotic solvent. Solvents which are suitable include chloroform, carbon tetrachloride, 1,1-dichloroethane, toluene, hexane, and preferably 1,2-dichloroethane. The mode of addition of the reactants is not critical in carrying out the process. For example, a solution or suspension of a phenoxazine or acridan and a carboxamide in 1,2-dichloroethane can be added to a solution of phosphorus oxychloride in 1,2-dichloroethane or the sequence of addition may be reversed and phosphorus oxychloride neat or dissolved in 1,2-dichloroethane can be added to a solution of the carboxamide and the phenoxazine or acridan. Alternatively, phosphorus oxychloride can be first added to the phenoxazine or acridan reactant and a carboxamide reactant then added. Another suitable adaptation of the process is the combination of phosphorus oxychloride with a carboxamide and the addition of this mixture to the heterocyclic phenoxazine or acridan reactant. Combination of the reactants provides an exothermic reaction and external cooling can be employed to moderate the reaction, although, this is not necessary for the successful completion of the reaction. The reaction of the carboxamide with the heterocyclic phenoxazine or acridan reactant takes place in a facile manner when the reactants are combined and generally does not require prolonged heating for the formation of the substances of Formula I. Although the reaction may be carried out at a temperature of about 0°–100°C., it is generally preferred to slowly add the phosphorus oxychloride to the heterocyclic phenoxazine or acridan reactant at a temperature in the range of from about 25°–35°C. with efficient stirring followed by a 15 hr. stirring period at room temperature before isolating the product.

Illustrative of the preferred method for preparation of the compounds of Formula I is addition of phosphorus oxychloride to a mixture of phenoxazine and 2-pyrrolidinone in 1,2-dichloroethane at 25°C. employing equimolar amounts of reactants to provide after stirring for 15 hr., 10-(1-pyrrolin-2-yl)phenoxazine.

The substances of Formula I are new chemical substances and have utility as pharmacological agents. They are particularly useful for their smooth muscle relaxant effects exhibiting papaverine-like activity. Apart from smooth muscle relaxant activity, the amidines of Formula I have, in some instances, significant antithrombogenic properties as demonstrated by the ability to inhibit platelet aggregation caused by the addition of adenosine diphosphate or collagen to human or rabbit platelet rich plasma.

Smooth muscle relaxant activity of the amidines of Formula I can be measured in standard and accepted in vitro and in vivo pharmacological tests. One such test is carried out essentially as follows. A segment of the rabbit ileum is suspended in oxygenated Tyrode's solution and affixed to a tension transducer for electronic recording of isometric contractions. After control responses to a standard dose of a spasmogen such as barium chloride (0.25 mg./ml.) are established, the imidoylphenoxazine or imidoylacridan is added and response to the spasmogen, in the presence of the heterocyclic amidine test agent, again determined. Test compound effect is measured as a percentage reduction in the response to the spasmogen in the presence of the test compounds, from the mean control response. A minimum of three trials is carried out at each of 2 to 5 different concentrations of test compound. The data obtained is expressed in log dose response curves and estimates therefrom of the $EC_{50}$ or $EC_{75}$ (concentration causing 50% or 75% reduction in the response of the tissue to the spasmogen).

The imidoylphenoxazines and imidoylacridans of the present invention have substantial activity in this test. With respect to potency, the substances of Formula I are equal to or have greater potency than papaverine in this test. As might be expected, certain of the compounds are more active than others. For example, 9,9-dimethyl-10-(5-methyl-1-pyrrolin-2-yl)acridan hydrochloride has an antispasmodic potency of 2 to 10 times that of papaverine. Compounds such as:

10-[2-(1-pyrrolinyl)]acridan,
10-[2-(5-methyl-1-pyrrolinyl)]acridan,
10-[2-(5,5-dimethyl-1-pyrrolinyl)]acridan,
10-[(3,4,5,6-tetrahydro-2-pyridyl)]acridan,
10-isopropyliminomethyl)acridan,
10-(5-methyl-1-pyrrolin-2-yl)phenoxazine, are equal in potency to papaverine in the foregoing in vitro test.

In the guinea pig isolated trachea smooth muscle preparation, 10-(5-methyl-1-pryyolin-2-yl)phenoxazine was 2.8 times more potent than aminophylline, a well-known smooth muscle relaxant.

Apart from smooth muscle relaxant activity, some of the amidine heterocyclics of Formula I are antithrombogenic agents as demonstrated in such standard antithrombogenic tests as described by Born, Nature, 194, 927 (1962) and O'Brien, J. Clin, Path., 15, 446 (1962).

The amidines of Formula I and non-toxic pharmaceutically acceptable salts thereof may be administered to mammals either singly or in combination with other pharmacological active ingredients. Routes of administration include parenteral as well as oral. Pharmacological effects, particularly smooth muscle relaxant activity, are obtained at non-toxic effective doses of the compounds of Formula I ranging from about 0.01 to 10 mg./kg. body weight. With respect to total daily dose, optimum smooth muscle relaxant effects are obtained at non-toxic effective doses of the compounds of Formula I ranging from about 0.05 to 100 mg./kg. body weight. It is to be understood that the term "non-toxic effective dose" as used herein refers to the quantity of active ingredient necessary to produce the desired therapeutic effect without causing any harmful or deleterious side effects. Whether singly or in combination, the substances of Formula I may be used in the usual pharmaceutical forms.

Oral toxicity values ($LD_{50}$) of the substances of Formula I in mice range from about 200 to 1000 mg./kg. of body weight. For instance, the $LD_{50}$ value (mg./kg. body weight) is 250–500 for 10-[2-(5-methyl-1-pyrrolinyl)]acridan hydrochloride; 100 for 10-[2-(5,5-dimethyl-1-pyrrolinyl)]acridan hydrochloride; 200 for 10(isopropyliminomethyl)acridan and; 250–500 for 9,9-dimethyl-10-(5-methyl-1-pyrrolin-2-yl)acridan hydrochloride.

The compounds of the present invention can be formulated according to conventional pharmaceutical practice to provide pharmaceutical compositions of unit dosage form which may include, for example, tablets, pills, capsules, powders, granules, emulsions, suspensions, and the like. The solid preparations contain the active ingredient in admixture with non-toxic pharmaceutical excipients such as inert diluents, for example calcium carbonate, sodium carbonate, lactose, calcium phosphate or sodium phosphate; granulating an disintegrating agents, for example maize, starch or alginic acid; binding agents, for example starch, gelatin or accacia; and lubricating agents, for example magnesium stearate, stearic acid or talc. The tablets may be uncoated or they may be coated by known techniques so as to defy disintegration and absorption in the gastrointestinal tract and thereby provide a sustained action over a longer period.

Liquid preparations suitable for parenteral administration include solutions, suspensions, or emulsions of the compounds of Formula I. The aqueous suspensions of the pharmaceutical dosage forms of the compunds of Formula I contain the active ingredient in admixture with one or more non-toxic pharmaceutical excipients known to be suitable in the manufacture of aqueous suspensions. Suitable excipients are, for example, suspending agents such as sodium carboxymethylcellulose, methylcellulose, hydroxypropylmethylcellulose, sodium alginate, polyvinylpyrrolidone, gum tragacanth and gum accacia. Suitable dispersing or wetting agents are naturally occurring phosphatides, for example lecthin, polyoxyethylene stearate.

Non-aqueous suspensions may be formulated by suspending the active ingredient in a vegetable oil, for example arachis oil, olive oil, sesame oil or coconut oil, or in a mineral oil, for example liquid paraffin. The suspensions may contain a thickening agent such as bees wax, hard paraffin or cetyl alcohol. Sweetening and flavoring agents generally used in pharmaceutical compositions may also be included such as saccharin, sodium cyclamate, sugar and caramel to provide a palatable oral preparation. The compositions may also contain other additional absorbing agents, stabilizing agents, weighing agents, and buffers.

The following examples further illustrate the present invention and will enable others skilled in the art to understand it more completely. It is to be understood, however, that the invention is not limited solely to the particular examples given below.

In regard to "NMR" data, the following notations are employed: $s$ = singlet, $d$ = doublet, $dd$ = doublet of doublets, $t$ = triplet, $s$-$7$ = septet, $m$ = multiplet, $bs$ = broad singlet. The solvent and internal reference peak, e.g., TMS (tetramethylsilane) is also given.

EXAMPLE 1

Phosphorus oxychloride (3.8 g., 0.025 mole) is added in one portion to a mixture of phenoxazine (4.6 g., 0.025 mole) and 2-pyrrolidinone (2.1 g., 0.025 mole) in 50 ml. of 1,2-dichloroethane at 25°C. After stirring the reaction mixture for 15 hr., the reaction mixture is quenched in a mixture of 30 ml. of 5N sodium hydroxide and 30 g. of crushed ice. The organic layer is separated, extracted with 100 ml. of 1.5N hydrochloric acid, made basic with sodium hydroxide and extracted with ether. After drying the ethereal extract over magnesium sulfate and concentrating, the residue thus obtained is crystallized from n-heptane to provide 4.2 g. of 10-(1-PYRROLIN-2-YL)PHENOXAZINE free base, m.p. 110°–113°C. The free base taken up in ethanol, acidified with ethanolic hydrogen chloride and diluted with ether provides a 37% yield of 10-(1-PYRROLIN-2-YL)PHENOXAXINE HYDROCHLORIDE as a monohydrate, m.p. 214°–217°C. (corr.).

Analysis. Calcd. for $C_{16}H_{14}N_2O \cdot HCl \cdot H_2O$ (percent): C, 63,05; H, 5.62; N, 9.19; Cl, 11.64. Found (percent): C, 62.92; H, 5.66; N, 9.35; Cl, 11.34.

NMR delta (ppm) (DMSO-$D_6$, TMS reference): 2.13$m$, 3.27$t$(7.2), 3,38$s$, 3.75$t$ (7.0), 7.3$m$, 7.7$m$, 10.63$bs$.

EXAMPLE 2

Reaction of phenoxazine with 5-methyl-2-pyrrolidinone according to the procedure of Example 1 affords the free base 10-(5-METHYL-1-PYRROLIN-2-YL)PHENOXAZINE, m.p. 135°–137°C., from n-heptane. Conversion of the free base to the hydrochloride salt provides 10-(5-METHYL-1-PYRROLIN-2-YL)PHENOXAZINE HYDROCHLORIDE, m.p. 229.5°–236.0°C. (dec.) (corr.), in a 57% overall yield.

Analysis. Calcd. for $C_{17}H_{16}N_2O \cdot HCl$ (percent): C, 67.88; H, 5.70; N, 9.32; Cl, 11.78. Found (percent): C, 67.79; H, 5.71; N, 9.39; Cl, 11.75.

NMR delta (ppm)(CDCl$_3$, TMS reference): 1.57$d$(6.3), 2.22$m$, 3,27$m$, 4.54$m$, 7.2$m$, 7.8$m$, 11.65$bs$.

EXAMPLE 3

Reaction of phenoxazine, 5,5-dimethyl-2-pyrrolidinone and phosphorus oxychloride according to the procedure of Example 1 provides the free base 10-(5,5-DIMETHYL-1-PYRROLIN-2-YL)-PHENOXAZINE, m.p. 148°–150°C. Conversion of the free base to the hydrochloride salt affords 10-(5,5-DIMETHYL-1-PYRROLIN-2-YL)PHENOXAZINE HYDROCHLORIDE, m.p. 239°–242.5°C. (corr.), in a 48% overall yield.

Analysis. Calcd. for $C_{18}H_{18}N_2O \cdot HCl$ (percent): C, 68.67; H, 6.08; N, 8.90; Cl, 11.27. Found (percent): C, 68.50; H, 6.21; N, 8.75; Cl, 11.24.

NMR delta (ppm)(CDCl$_3$, TMS reference): 1.69$s$, 2.05$t$ (7.5), 3.26$t$ (7.5), 7.2$m$, 7.8$m$, 11.80$bs$.

EXAMPLE 4

Reaction of 2-(trifluoromethyl)phenoxazine, 2-pyrrolidinone and phosphorus oxychloride according to the procedure of Example 1 provides the free base 10-(1-PYRROLIN-2-YL)-2-(TRIFLUOROMETHYL)PHENOXAZINE as a distillable oil, b.p. 140°–146°C. at 0.1 mm Hg. Conversion of the free base to the hydrochloride salt affords 10-(1-PYRROLIN-2-YL)-2-(TRIFLUOROMETHYL)PHENOXAZINE HYDROCHORIDE, m.p. 219.5°–222.5°C. (dec.)-(corr.), in a 62% overall yield by triturating with warm benzene.

Analysis. Calcd. for $C_{17}H_{13}F_3N_2O \cdot HCl$ (percent): C, 57.55; H, 3.98; N, 7.90; Cl, 9.99. Found (percent): C, 57.60; H, 4.14; N, 7.63; Cl, 9.77.

NMR delta (ppm)(CDCl$_3$, TMS reference): 2.27$m$, 3.31$t$ (7.4), 4.11$t$ (7.0), 7.2$m$, 7.9$m$.

EXAMPLE 5

Reaction of 2-(trifluoromethyl)phenoxazine, 5-methyl-2-pyrrolidinone and phosphorus oxychloride according to the procedure of Example 1 provides the free base 10-(5-METHYL-1-PYRROLIN-2-YL)-2-(TRIFLUOROMETHYL)PHENOXAZINE as a distillable oil, b.p. 145°–152°C. at 0.03 mm Hg. Conversion of the free base to the hydrochloride salt affords 10-(5-METHYL-1-PYRROLIN-2-YL)-2-(TRIFLUOROMETHYL)PHENOXAZINE HYDROCHLORIDE, m.p. 192.5°–195.5°C. (dec.)(corr.)., in a 45% overall yield.

Analysis. Calcd. for $C_{18}H_{15}F_3N_2O \cdot HCl$ (percent): C, 58.62; H, 4.37; N, 7.60; Cl, 9.61. Found (percent): C, 58.61; H, 4.42; N, 7.41; Cl, 9.31.

NMR delta (ppm)(CDCl$_3$, TMS reference): 1.57$d$ (6.2), 1.97$m$, 3.26$m$, 4.54$m$, 7.3$m$, 8.0$m$.

EXAMPLE 6

Reaction of 2-(trifluoromethyl)phenoxazine, 5,5-dimethyl-2-pyrrolidinone and phosphorus oxychloride according to the procedure of Example 1 provides the free base 10-(5,5-DIMETHYL-1-PYRROLIN-2-YL)-2-(TRIFLUOROMETHYL)PHENOXAZINE, m.p. 64°–67°C. Conversion of the free base to the hydrochloride salt affords 10-(5,5-DIMETHYL-1-PYRROLIN-2-YL)-2-(TRIFLUOROMETHYL)PHENOXAZINE HYDROCHLORIDE, m.p. 204.5°–207.5°C. (dec.) (corr.), in a 30% overall yield.

Analysis. Calcd. for $C_{19}H_{17}F_3N_2O \cdot HCl$ (percent): C, 59.61; H, 4.74; N, 7.32; Cl, 9.26. Found (percent): C, 59.37; H, 4.78; N, 7.12; Cl, 9.11.

NMR delta (ppm) (CDCl$_3$, TMS reference): 1.70$s$, 2.10$t$ (7.5), 3.27$t$ (7.5), 7.4$m$, 12.00$bs$.

EXAMPLE 7

Reaction of 2-chlorophenoxazine, 2-pyrrolidinone, and phosphorus oxychloride according to the procedure of Example 1 provides the free base 2-CHLORO-10-(1-PYRROLIN-2-YL)PHENOXAZINE as a distillable oil, b.p. 150°–165°C. at 0.1 mm Hg. Conversion of the free base to the hydrochloride salt affords 2-CHLORO-10-(1-PYRROLIN-2-YL)-PHENOXAZINE HYDROCHLORIDE, m.p. 209.5°–213.5°C. (corr.), in a 40% overall yield.

Analysis. Calcd. for $C_{16}H_{13}ClN_2O\cdot HCl$ (percent): C, 59.82; H, 4.39; N, 8.72; Cl, 22.09. Found (percent): C, 59.71; H, 4.44; N, 8.50; Cl, 21.97.

NMR delta (ppm)(DMSO-$d_6$, TMS reference): 2.13$m$, 3.27$t$ (7.5), 3.75$t$ (7.0), 7.3$m$, 7.7$m$, 10.67$bs$.

EXAMPLE 8

Reaction of 2-chlorophenoxazine, 5-methyl-2-pyrrolidinone and phosphorus oxychloride according to the procedure of Example 1 provides the free base 2-CHLORO-10-(5-METHYL-1-PYRROLIN-2-YL)-PHENOXAZINE as a distillable oil, b.p. 150°–170°C. at 0.1 mm Hg. Conversion of the free base to the hydrochloride salt affords 2-CHLORO-10-(5-METHYL-1-PYRROLIN-2-YL)PHENOXAZINE HYDROCHLORIDE, m.p. 213.5°–215.5°C., as a crystalline solid in a 34% overall yield by refluxing with benzene.

Analysis. Calcd. for $C_{17}H_{15}ClN_2O\cdot HCl$ (percent): C, 60.90; H, 4.81; N, 8.36; Cl, 21.16. Found (percent): C, 60.79; H, 5.01; N, 8.28; Cl, 20.78.

NMR delta (ppm)(CDCl$_3$, TMS reference): 1.58$d$ (6.2), 2.23$m$, 3.34$m$, 4.58$m$, 7.2$m$, 7.8$m$, 12.03$bs$.

EXAMPLE 9

Reaction of 2-chlorophenoxazine, 5,5-dimethyl-2-pyrrolidinone and phosphorus oxychloride according to the procedure of Example 1 provides 2-CHLORO-10-(5,5-DIMETHYL-1-PYRROLIN-2-YL)-PHENOXAZINE, m.p. 118°–120°C., from ethanol.

Analysis. Calcd. for $C_{18}H_{17}ClN_2O$ (percent): C, 69.11; H, 5.48; N, 8.96; Cl, 11.34. Found (percent): C, 68.89; H, 5.41; N, 8.85; Cl, 11.01.

NMR delta (ppm)(CDCl$_3$, TMS reference): 1.28$s$, 1.78$t$ (7.5), 2.81$t$ (7.5), 6.9$m$, 7.25$m$, 7.53$dd$ (1.8, 0.5).

EXAMPLE 10

Reaction of 4-chlorophenoxazine, 5-methyl 2-pyrrolidinone and phosphorus oxychloride according to the procedure of Example 1 provides the free base 4-CHLORO-10-(5-METHYL-1-PYRROLIN-2-YL)PHENOXAZINE, m.p. 120°–122°C., from ethanol. Conversion of the free base to the hydrochloride salt affords 4-CHLORO-10-(5-METHYL-1-PYRROLIN-2-YL)PHENOXAZINE HYDROCHLORIDE, m.p. 228°–230°C., (dec.) (corr.), by trituration with hot benzene.

Analysis. Calcd. for $C_{17}H_{15}ClN_2O\cdot HCl$ (percent): C, 60.90; H, 4.81; N, 8.36; Cl, 21.16. Found (percent): C, 60.85; H, 4.90; N, 8.22; Cl, 20.94.

NMR delta (ppm)(CDCl$_3$, TMS reference): 1.57$d$ (6.4), 2.17$m$, 3.30$m$, 4.60$m$, 7.3$m$, 7.9$m$, 11.70$bs$.

EXAMPLE 11

Reaction of 2-methoxyphenoxazine, 5-methyl-2-pyrrolidinone and phosphorus oxychloride according to the procedure of Example 1 provides the free base 2-METHOXY-10-(5-METHYL-1-PYRROLIN-2YL)-PHENOXAZINE as an oil. Conversion of the free base to the hydrochloride salt affords 2METHOXY-10-(5-METHYL-1-PYRROLIN-2-YL)-PHENOXAZINE HYDROCHLORIDE, m.p. 223.5°–224.5°C. (dec.)-(corr.), as the hemihydrate by trituration with acetone.

Analysis. Calcd. for $C_{18}H_{18}N_2O_2\cdot HCl\cdot\frac{1}{2}$ $H_2O$ (percent): C, 63.62; H, 5.92; N, 8.25; Cl, 10.42. Found (percent): C, 63.96; H, 6.40; N, 7.99; Cl, 10.05.

NMR delta (ppm)(D$_2$O, HDO reference): 1.18$d$, (6.1), 2.18$m$, 2.77$m$, 3.81$s$, 3.95$m$, 7.1$m$.

EXAMPLE 12

Reaction of phenoxazine, 2-piperidone, and phosphorus oxychloride according to the procedure of Example 1 provides 10-(3,4,5,6-TETRAHYDRO-2-PYRIDYL)PHENOXAZINE HYDROCHLORIDE, m.p. 218.5°–221°C. (corr.), in a 27% overall yield from absolute ethanol.

Analysis. Calcd. for $C_{17}H_{16}N_2O\cdot HCl$ (percent): C, 67.88; H, 5.70; N, 9.30; Cl, 11.78. Found (percent): C, 67.51; H, 5.68; N, 9.19; Cl, 11.69.

NMR delta (ppm)(CDCl$_3$, TMS reference): 1.87$m$, 2.84$m$, 3.83$m$, 7.2$m$, 7.7$m$, 10.77$bs$.

EXAMPLE 13

Reaction of acridan, 2-pyrrolidinone and phosphorus oxychloride according to the procedure of Example 1 provides the free base 10-[2-(1-PYRROLINYL)]ACRIDAN, m.p. 130°–132°C., from n-heptane. Conversion of the free base of the hydrochloride salt affords 10-[2-(1-PYRROLINYL)]ACRIDAN HYDROCHLORIDE as the hemihydrate, m.p. 251°–252°C. (dec.)(corr.), from ethanol-ether in a 42% overall yield.

Analysis. Calcd. for $C_{17}H_{16}N_2\cdot HCl\cdot\frac{1}{2}$ $H_2O$ (percent): C, 69.50; H, 6.18; N, 9.53; Cl, 12.07. Found (percent): C, 69.74; H, 6.29; N, 9.50; Cl, 12.17.

NMR delta (ppm)(D$_2$O, HDO reference): 2.25$m$, 3.05$m$, 3.57$s$, 3.86$t$ (7.0), 7.4$m$.

EXAMPLE 14

Reaction of acridan, 5-methyl-2-pyrrolidinone and phosphorus oxychloride according to the procedure of Example 1 provides the free base 10-[2-(5-METHYL-1-PYRROLINYL)]ACRIDAN, m.p. 107°–109°C. Conversion of the free base to the hydrochloride salt affords 10-[2-(5-METHYL-1-PYRROLINYL)]ACRIDAN HYDROCHLORIDE, m.p. 203.5°–206°C. (dec.) (corr.), by trituration with hot benzene in a 33% overall yield.

Analysis. Calcd. for $C_{18}H_{18}N_2\cdot HCl$ (percent): C, 72.35; H, 6.41; N, 9.38; Cl, 11.86. Found (percent): C, 72.38; H, 6.46; N, 9.37; Cl, 11.67.

NMR delta (ppm)(D$_2$O, HDO reference): 1.26$d$ (6.3), 2.01$m$, 2.93$m$, 3.68$s$, 4.14$m$, 7.3$m$.

EXAMPLE 15

Reaction of acridan, 5,5-dimethyl-2-pyrrolidinone and phosphorus oxychloride according to the procedure of Example 1 provides the free base 10-[2-(5,5-DIMETHYL-1-PYRROLINYL)]-ACRIDAN, m.p. 84°–86°C. Conversion of the free base to the hydrochloride salt affords 10-[2-(5,5-DIMETHYL-1-PYRROLINYL)]ACRIDAN HYDROCHLORIDE, m.p. 266.5°–267°C. (dec.) (corr.), by triturating first with acetone and then crystallizing from ethanol-ether in a 31% overall yield.

Analysis. Calcd. for $C_{19}H_{20}N_2\cdot HCl$ (percent): C, 72.94; H, 6.77; N, 8.96; Cl, 11.33. Found (percent): C, 73.14; H, 6.64; N, 8.81; Cl, 11.31.

NMR delta (ppm)(D$_2$O, HDO reference): 1.39$s$, 2.01$t$ (7.5), 3.07$m$, 3.72$s$, 7.4$m$.

EXAMPLE 16

Reaction of acridan, 2-piperidone and phosphorus oxychloride according to the procedure of Example 1 provides the free base 10-(3,4,5,6-TETRAHYDRO-2-PYRIDYL)ACRIDAN as a distillable oil, b.p. 145°–150°C. at 0.15 mm Hg. Conversion of the free base to the hydrochloride salt affords 10-(3,4,5,5-TETRAHYDRO-2-PYRIDYL)ACRIDAN HYDROCHLORIDE as the hemihydrate, m.p. 190.5°–192.5°C. (corr.) by trituration with hot benzene in a 19% overall yield.

Analysis. Calcd. for $C_{18}H_{18}N_2 \cdot HCl \cdot \frac{1}{2} H_2O$ (percent): C, 70.23; H, 6.55; N, 9.10; Cl, 11.52. Found (percent): C, 70.12; H, 6.15; N, 9.16; Cl, 11.56.

NMR delta (ppm)($D_2O$, HDO reference(: 1.73$m$, 2.72$m$, 3.38$m$, 3.71$s$, 7.3$m$.

EXAMPLE 17

Reaction of acridan, isopropylformamide and phosphorus oxychloride accoridng to the procedure of Example 1 provides the free base 10-[(ISOPROPYLIMINO)METHYL]ACRIDAN, m.p. 149.5°–150.5°C. (corr.), from n-hexane.

Analysis, Calcd. for $C_{17}H_{18}N_2$ (percent): C, 81.56; H, 7.25; N, 11.19. Found (percent): C, 81.86; H, 7.23; N, 11.18.

NMR delta (ppm)($CDCl_3$, TMS reference): 1.23$d$, (6.3), 3.48$s$-7(6.3), 3.82$s$, 7.2$m$, 7.8$m$, 8.30$s$.

EXAMPLE 18

Reaction of 9,9-dimethylacridan, 5-methyl-2-pyrrolidinone and phosphorus oxychloride according to the procedure of Example 1 provides the free base 9,9-DIMETHYL-10-(5-METHYL-1-PYRROLIN-2-YL)ACRIDAN as a distillable oil, b.p. 160°–180°C. at 0.15 mm Hg. in 11% yield. Conversion of the free base to the hydrochloride salt affords 9,9-DIMETHYL-10-(5-METHYL-1-PYRROLIN-2-YL)ACRIDAN HYDROCHLORIDE, m.p. 232.5°–234.5°C. (dec.) (corr.), by trituration with hot benzene.

Analysis. Calcd. for $C_{20}H_{22}N_2 \cdot HCl$ (percent): C, 73.49; H, 7.09; N, 8.57; Cl, 10.85. Found (percent): C, 73.39; H, 7.04; N, 8.74; Cl, 10.63.

NMR delta (ppm)($DMSO-d_6$, TMS reference): 1.35$d$ (6.4), 1.59$s$, 1.75$m$, 3.32$m$, 4.36$m$, 7.6$m$, 10.63$bs$.

EXAMPLE 19

Reaction of the enumerated phenoxazines and carboxamides in the presence of phosphorus oxychloride according to the procedure of Example 1 provides the following amidine products of Formula I:

a. 3-chloro-10-(5-methyl-1-pyrrolin-2-yl)phenoxazine from 3-chlorophenoxazine and 5-methyl-2-pyrrolidione;

b. 2,3-dichloro-10-(5-methyl-1-pyrrolin-2-yl)phenoxazine from 2,3dichlorophenoxazine and 5-methyl-2 -pyrrolidione;

c. 3,4-dichloro-10-(5-methyl-1-pyrrolin-2-yl)phenoxazine from 3,4-dichlorophenoxazine and 5-methyl-2-pyrrolidinone;

d. 4-methoxy-10-(1-pyrrolin-2-yl)phenoxazine from 4-methoxyphenoxazine and 2-pyrrolidinone;

e. 4-isopropoxy-10-(1-pyrrolin-2-yl)phenoxazine from 4-isopropoxyphenoxazine and 2-pyrrolidinone;

f. 2-methyl-10-(1-pyrrolin-2-yl)phenoxazine from 2-methylphenoxazine and 2-pyrrolidinone;

g. 4-methyl-10-(1-pyrrolin-2-yl)phenoxazine from 4-methylphenoxazine and 2-pyrrolidinone;

h. 4-n-butyl-10-(1-pyrrolin-2-yl)phenoxazine from 4-n-butylphenoxazine and 2-pyrrolidinone;

i. 2-bromo-10-(1-pyrrolin-2-yl)phenoxazine from 2-bromophenoxazine and 2-pyrrolidinone;

j. 10-(4-methyl-1-pyrrolin-2-yl)phenoxazine from phenoxazine and 4-methyl-2-pyrrolidinone;

k. 10-(5,5-di-n-butyl-1-pyrrolin-2-yl)phenoxazine from phenoxazine and 5,5-di-n-butyl-2-pyrrolidinone;

l. 10-[(methylimino)methyl]phenoxazine from phenoxazine and N-methylformamide;

m. 10-[(cyclopropylimino)methyl]phenoxazine from phenoxazine and N-cyclopropylformamide;

n. 10-[(cyclopentylimino)methyl]phenoxazine from phenoxazine and N-cyclopentylformamide;

o. 10-[(cyclohexylimino)methyl]phenoxazine from phenoxazine and N-cyclohexylformamide;

p. 10-[1-(1-cyclohexylimino)ethyl]phenoxazine from phenoxazine and N-cyclohexylacetamide;

q. 10-[1-(methylimino)ethyl]phenoxazine from phenoxazine and N-methylacetamide;

r. 4-chloro-10-[1-(methylimino)-2-methylpropyl]phenoxazine from 4-chlorophenoxazine and N-methyl-2-methylpropionamide;

s. 10-[1-(methylimino)-n-pentyl]phenoxazine from phenoxazine and n-methylvaleramide;

t. 10-(6-methyl-3,4,5-trihydro-2-pyridyl)phenoxazine from phenoxazine and 6-methyl-2-piperidone;

u. 10-(6,6-dimethyl-3,4,5-trihydro-2-pyridyl)-phenoxazine from phenoxazine and 6,6-dimethyl-2-piperidone;

v. 10-[7-(3,4,5,6-tetrahydro-2H-azepinyl)]-2-(trifluoromethyl)-phenoxazine from 2-(trifluoromethyl)-phenoxazine and 2-oxohexamethyleneimine.

EXAMPLE 20

Reaction of the enumerated acridan and carboxamide in the presence of phosphorus oxychloride according to the procedure of Example 1 provides the following amidine products of Formula I:

a. 2-methoxy-10-(1-pyrrolin-2-yl)acridan from 2-methoxyacridan and 2-pyrrolidinone;

b. 4-methoxy-10-[(methylimino)methyl]acridan from 4-methoxyacridan and N-methylformamide;

c. 2-chloro-10-[1-(methylimino)ethyl]acridan from 2-chloroacridan and N-methylacetamide;

d. 4-chloro-10-[(cyclopropylimino)methyl]acridan from 4-chloroacridan and N-cyclopropylacetamide;

e. 10-[(cyclohexylimino)methyl]-2-(trifluoromethyl)acridan from 2-(trifluoromethyl)acridan and N-cyclohexylformamide;

f. 10-[(isopropylimino)methyl]-4-(trifluoromethyl)acridan from 4-(trifluoromethyl)acridan and N-isopropylformamide;

g. 2-chloro-9,9-dimethyl-10-(5,5-dimethyl-1-pyrrolin-2-yl)-acridan from 2-chloro-9,9-dimethylacridan and 5,5-dimethyl-2-pyrrolidinone;

h. 9,9-dimethyl-10-(4-methyl-1-pyrrolin-2-yl)-2-(trifluoromethyl)acridan from 9,9-dimethyl- 2(trifluoromethyl)acridan and 4-methyl-2-pyrrolidinone;

i. 9,9-dimethyl-4-methoxy-10-(3,4,5,6-tetrahydro-2-pyridyl)-acridan from 9,9-dimethyl-4-methoxyacridan and 2-piperidone;

j. 2-methyl-10-(6-methyl-3,4,5-trihydro-2-pyridyl)acridan from 2-methylacridan and 6-methyl-2-piperidone;

k. 4-methyl-10-(6,6-dimethyl-3,4,5-trihydro-2-pyridyl)acridan from 4-methylacridan and 6,6-dimethyl-2-piperidone;

l. 4-n-butyl-10-[7-(3,4,5,6-tetrahydro-2H-azepinyl)]acridan from 4-n-butylacridan and 2-oxohexamethyleneimine;

m. 9-methyl-10-(1-pyrrolin-2-yl)-2-(trifluoromethyl)acridan from 9-methyl-2-(trifluoromethyl)acridan and 2-pyrrolidinone;

n. 9-ethyl-9-methyl-10-(1-pyrrolin-2-yl)acridan from 9-ethyl-9-methylacridan and 2-pyrrolidinone;

o. 9,9-di-n-butyl-10-(1-pyrrolin-2-yl)acridan from 9,9-di-n-butylacridan and 2-pyrrolidinone.

While specific embodiments are disclosed in the foregoing specification, it will be appreciated that other modifications may be made without departing from the spirit and scope of the appended claims.

What is claimed is:

1. A compound selected from the group consisting of 10-imidoylacridans having the formula

[structure: acridan core with X at 9-position, Y substituent, N at 10-position bearing group A]

and a non-toxic pharmaceutically acceptable acid addition salt thereof wherein

X represents a divalent methylene radical of the formula $-C(Z_1Z_2)-$ wherein $Z_1$ and $Z_2$ are independently selected from hydrogen or straight chain lower alkyl of from 1 to 4 carbon atoms inclusive;

Y represents hydrogen, trifluoromethyl, halogen, dihalogen, lower alkyl of 1 to 4 carbon atoms inclusive, lower alkoxy of 1 to 4 carbon atoms inclusive; and is selected from the group consisting of $$-\underset{R_2}{\overset{}{C}}=N-R_1 \quad \text{and} \quad -CH=N\diagup\underset{(CH_2)_n}{\overset{R_3}{\diagdown}}R_4$$

wherein $R_1$ is lower alkyl of 1 to 4 carbon atoms inclusive or cycloalkyl of 3 to 6 carbon atoms inclusive;

$R_2$ is hydrogen or lower alkyl of 1 to 4 carbon atoms inclusive;

$R_3$ and $R_4$ are independent members selected from the group consisting of hydrogen or lower alkyl of 1 to 4 carbon atoms inclusive;

n is an integer of 3 to 5.

2. A compound according to claim 1 being a member selected from the group consisting of 10-[2-(1-pyrrolinyl)]acridan or a pharmaceutically acceptable acid addition salt thereof.

3. A compound according to claim 1 being a member selected from the group consisting of 10-[2-(5-methyl-1-pyrrolinyl)]acridan or a pharmaceutically acceptable acid addition salt thereof.

4. A compound according to claim 1 being a member selected from the group consisting of 10-[2-(5,5-dimethyl-1-pyrrolinyl)]acridan or a pharmaceutically acceptable acid addition salt thereof.

5. A compound according to claim 1 being a member selected from the group consisting of 10-(3,4,5,6-tetrahydro-2-pyridyl)acridan or a pharmaceutically acceptable acid addition salt thereof.

6. A compound according to claim 1 being a member selected from the group consisting of 10-[(isopropylimino)methyl]acridan or a pharmaceutically acceptable acid addition salt thereof.

7. A compound according to claim 1 being a member selected from the group consisting of 9,9-dimethyl-10-(5-methyl-1-pyrrolin-2-yl)-acridan or a pharmaceutically acceptable acid addition salt thereof.

* * * * *

UNITED STATES PATENT OFFICE
CERTIFICATE OF CORRECTION

Patent No. 3,962,252                    Dated    June 8, 1976

Inventor(s)    Yao Hua Wu et al.

It is certified that error appears in the above-identified patent and that said Letters Patent are hereby corrected as shown below:

Column 2, line 5, and column 14, correct the second formula to read as follows:

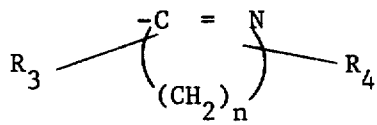

Column 3, lines 15 and 16, delete "reference):" and in its place insert --of--.

Column 3, line 30, correct the formulas to read as follows:

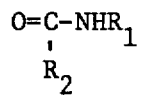     and     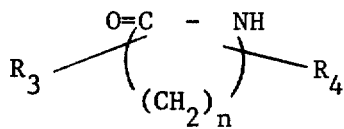

III                                  IV

UNITED STATES PATENT OFFICE
CERTIFICATE OF CORRECTION

Patent No. 3,962,252  Dated June 8, 1976

Inventor(s) Yao Hua Wu et al.

It is certified that error appears in the above-identified patent and that said Letters Patent are hereby corrected as shown below:

Column 13, line 41, after "and" insert -- A --.

Signed and Sealed this

Thirteenth Day of December 1977

[SEAL]

Attest:

RUTH C. MASON
Attesting Officer

LUTRELLE F. PARKER
Acting Commissioner of Patents and Trademarks